(12) United States Patent
Sakoda

(10) Patent No.: US 6,395,747 B1
(45) Date of Patent: May 28, 2002

(54) REMEDIES FOR MULTIPLE SCLEROSIS

(75) Inventor: Saburo Sakoda, Osaka (JP)

(73) Assignees: Sauro Sakoda, Osaka; Kyorin Pharmaceutical Co., Ltd., Tokyo, both of (JP)

( * ) Notice: Subject to any disclaimer, the term of this patent is extended or adjusted under 35 U.S.C. 154(b) by 0 days.

(21) Appl. No.: 09/762,616

(22) PCT Filed: Aug. 10, 1998

(86) PCT No.: PCT/JP98/03548

§ 371 (c)(1),
(2), (4) Date: Feb. 8, 2001

(87) PCT Pub. No.: WO00/09127

PCT Pub. Date: Feb. 24, 2000

(51) Int. Cl.[7] .............................................. A61K 31/435
(52) U.S. Cl. ...................................................... 514/300
(58) Field of Search .......................................... 514/300

(56) References Cited

U.S. PATENT DOCUMENTS 5,672,622 A * 9/1997 Hedgepath et al. ......... 514/424

OTHER PUBLICATIONS

Murashima et al, Inhibitory Effect of Ibudilast (KC–404) on Cyclic Nucleotide Phosphodiesterases, Jpn. Phamacol. Ther., vol. 26 No. 1. pp. 41–45 (1998).*

* cited by examiner

*Primary Examiner*—Bernard Dentz
(74) *Attorney, Agent, or Firm*—Reed Smith LLP

(57) ABSTRACT

A medicine for treatment of multiple sclerosis comprising, as an effective component, ibudilast represented by the chemical formula (1) below. Ibudilast is effective to experimental autoimmune encephalomyelitis by oral administration, and is effective to multiple sclerosis which is a disease of a central nervous system.

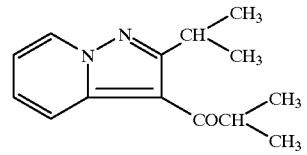

(1)

1 Claim, 3 Drawing Sheets

[Clinical Score]

Score 0: No symptom (normal)
Score 0.5: Mild paresis of the tail
Score 1: Limp tail
Score 2: Mild paraparesis of the hind limbs with unsteady gait
Score 3: Moderate paraparesis
Score 4: Paraplegia

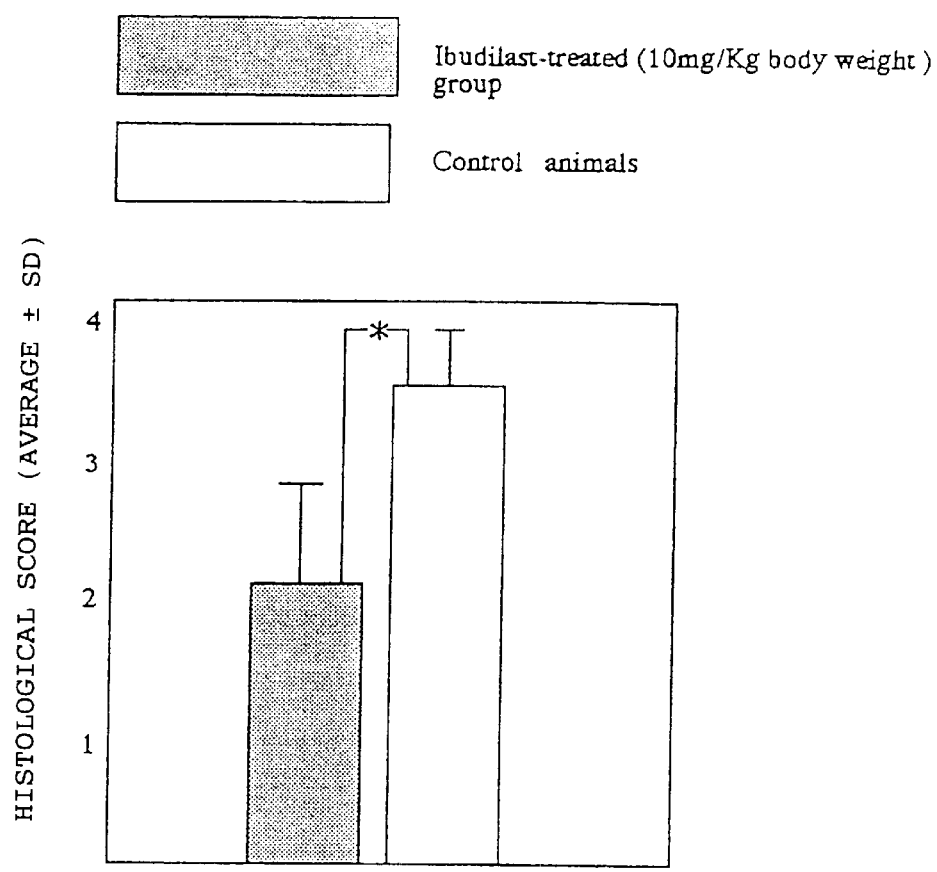

[Histological Score]
Score 0: Normal
Score 1: Inflammatory cell cuffing limited to the perivascular spaces
Score 2: A few infiltration of inflammatory cells into spinal cord parenchyma
Score 3: Considerable infiltration of inflammatory cells into spinal cord parenchyma
Score 4: Marked infiltration of inflammatory cells into spinal cord parenchyma with destruction of the gray matter

FIG. 3

REMEDIES FOR MULTIPLE SCLEROSIS

This application is a 371 of PCT/JP98/03548 filed Aug. 10, 1998.

TECHNICAL FIELD

The present invention relates to a novel use of a medicine for multiple sclerosis.

TECHNICAL BACKGROUND

Multiple sclerosis is a disease of the central nervous system, which is slowly progressive and is characterized by diffuse patches of demyelination in the brain and spinal cord, resulting in multiple and varied neurogic symptoms and signs, usually with repeated relapse and remission. The cause is unknown but an immunologic abnormality is suspected, with few clues presently indicating a specific mechanism (THE MERCK MANUAL, 16th EDITION, 1993 MERCK & CO.).

There are more multiple sclerosis cases in Europe and the United States than in Japan. In Japan, adrenocortical steroid, or vitamin $B_{12}$ is used for the therapy (Konnichi no Chiryo Shishin (TODAY'S THERAPY), 1995, Igaku Shoin K.K.). Myzoribine, which is an immunosuppressive agent, and interferon β1b are investigated as novel medicines (Asu no Shinyaku (New Medicine of Tomorrow), 1997, Technomic K.K.).

In Europe and the United States, where there are many patients with this disease, fundamental and clinical researches are being conducted actively. As the pharmacotherapy, interferon β is mainly investigated, and injectables of interferon β are supplied to clinical sites (SCRIP, No2223 p20 Apr. 15, 1997: SCRIP, No2227 p21 Apr. 29, 1997). In Europe and the United States, the interferon β is given, to patients with relapsing-remitting multiple sclerosis, subcutaneously in high doses every other day to decrease the frequency of neurological exacerbation (THE MERCK MANUAL, 16th EDITION, 1993, MERCK & CO.,INC). However, since the interferon β is expensive and should be administered for a long-term, such medical treatment becomes costly. So as to gain the higher medicinal compliance ratio, and less frequency of hospital attendance for higher quality of life of the patient, an orally administrable medicine has been desired.

Adrenocortical steroid can be administered orally for the therapy. However, the use of the adrenocortical steroid should be limited to remission of acute attack or the like since long-term of administration thereof may cause a side effect.

In recent years, pentoxifylline, and rolipram, which are respectively an inhibitor against an intracellular enzyme phosphodiesterase (hereinafter referred to as PDE), are reported to be possibly effective (Rott et al., Eur.J.Immunol., 23,p1745,1993; Nataf et al., Acta Neurol.Scand., 88,p97, 1993; Genain et al., Proc.Natl.Acad.Sci., 92,3601,1995; Sommer et al., Nature Med., 1,p244,1995; Jung et al., J.Neuroimmunol., 68,p1, 1996; and Okuda et al., Immunopharmacol., 35,p141,1996). Oral administration of pentoxifylline was practically tested by multiple sclerosis patients, but the results of the evaluation for the medical effectiveness are not consistent (Rieckmann et al., J.Neurol., 242(Suppl.2),S112,1995; van Oosten et al., J.Neurol., 242 (Suppl. 2),S-119,1995; Myers et al., Neurol., 45(Suppl.4), A419,1995); Rieckmann et al., J.Neuroimmunol., 64,p193, 1996). Therefore, a medicine is demanded increasingly which is more effective and can be administered orally.

With the aforementioned background, a medicine for multiple sclerosis is demanded which is suitable for oral administration and is effective by a clinically applicable amount of dosage.

DISCLOSURE OF THE INVENTION

The inventor of the present invention, after comprehensive studies to find a useful compound as a medicine for multiple sclerosis, has found that ibudilast attains the above object, and has completed the present invention.

The present invention relates to a medicine for multiple sclerosis, comprising ibudilast represented by the chemical formula (1) below as the effective component:

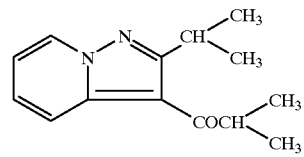

(1)

The present invention relates also to a therapeutic treatment of multiple sclerosis by oral administration of a medicine containing ibudilast as an effective component.

The inventor of the present invention has found first the effect of ibudilast, for treatment of multiple sclerosis. The ibudilast is used widely in Japan as a medicine, and a large amount of safety information are available.

The ibudilast is a known compound represented by the above chemical formula (1) (Japanese Patent Publication Sho-52-29318 (1977), U.S. Pat. No. 3,850,941 (1974), etc.), developed by Kyorin Pharmaceutical Co., Ltd. as a medicine, and approved by Japanese Ministry of Health and Welfare for production and sale on January 1989. Since then, the ibudilast is widely used as a medicine for bronchial asthma and a cerebral circulation-improving agent. The known activities of the ibudilast includes potentiation of action of prostacycline (Onoue et al., Gen.Pharmacol., 23,p1093,1992) and resulting increase of regeional cerebral blood blow (Kudo et al., Folia Pharmacol. Jap.,85,p435, 1995); leukotriene antagonism (Sato et al., Gen.Pharmacol., 17,p287, 1986; Ohashi et al., Int.Arch.Allergy.Immunol., 101,p.288,1993); suppression of leukotriene liberation (Tamura et al., Basic and Clinical Report, 20,p181,1986); inhibition of PDE (Souness et al., Brit.J.Pharmacol., 111, p1081,1994); and so forth. However, nothing has been known about the effectiveness thereof on the multiple sclerosis.

Ibudilast can be administered to humans in a pharmaceutically known formulation form and a dosing method, for example, in a form of powder, tablets, capsules, fine grains, granules, injection, solution, ointment, cataplasm, and so forth orally or parentally. An oral formulation is preferred in consideration of ease in use by a patient. The amount of the dosage of ibudilast depends on the age and body weight of the patient, conditions of the disease, and the method of the dosing. The amount of the oral dosage ranges preferably from 100 to 200 mg, more preferably from 10 to 60 mg in one dose, and dosing of two or three times per day is preferred.

BRIEF DESCRIPTION OF THE INVENTION

FIG. 3 is a graph showing the evaluation results of average histologic score in Example 2.

EXAMPLES

The effectiveness of ibudilast against multiple sclerosis is described in detail by reference to Examples. Rats of an experimental autoimmune encephalomyelitis (hereinafter referred to as EAE) model were used for evaluation of effect of ibudilast for amelioration of multiple sclerosis (Example 1). The EAE model is generally used as an animal model for multiple sclerosis (Ruddle et al., J.Exp.Med., 172,p1193, 1990; Powell et al., Int.Immunol., 2,p539,1990; Olsson et al., J.Neuroimmunol., 40,p211, 1992; Kartin et al., J.Exp.Med., 180,p2227,1994; and Selmaj et al., ANN.Neurol., 30,p694,1991). Further, pathological evaluation was conducted for confirming the ameliorating effect for the disease condition (Example 2). As the results, ibudilast was found to have ameliorating effect for the disease of the EAE model. The effect of ibudilast was confirmed histopathologically also.

Example 1

The disease ameliorating effect of ibudilast was investigated using rats of a multiple sclerosis model (EAE model).
(1) Experimental Animal: DA Strain Rats (6 Rats in Each Group)
(2) Preparation of Model The rats were injected subcutaneously with a Freund's complete adjuvant containing H37Ra Mycobacterium tuberculosis, and Myelin basic protein (MBP).

The rats of the control group were injected merely with the Freund's complete adjuvant. The experiment was conducted by taking as the reference the disease development in the control group. The observation was conducted until 18 days after the disease onset.
(3) Method of Dosing Ibudilast was administered through a feeding tube at a dosage of 2 mg/kg, or 10 mg/kg once a day. The dosing was continued from the time before disease onset to the time after the disease onset. The control group was dosed with physiological saline in the same manner.
(4) Evaluation of Effect The disease ameliorating effect (clinical effect) of ibudilast was scored and evaluated with the evaluation standard below.

Score 0: No symptom (normal)

Score 0.5: Mild paresis of the tail

Score 1: Limp tail

Score 2: Mild paraparesis of the hind limbs with unsteady gait

Score 3: Moderate paraparesis

Score 4: Paraplegia
(5) Results

Figure 1:
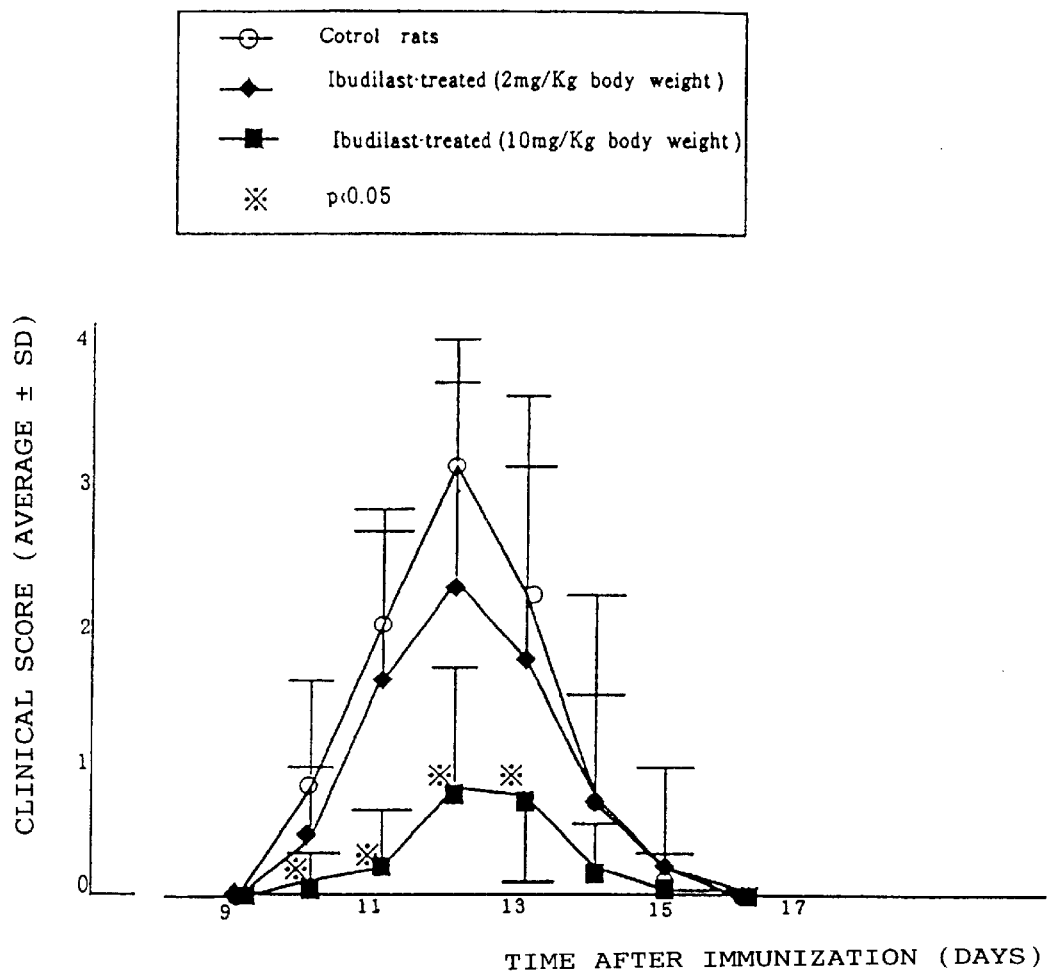
FIG. 1 is a graph showing the evaluation results by average clinical score for EAE model in Example 1 on each time after immunization.

In comparison with the control group, the 2 mg/kg ibudilast-treated group showed tendency of amelioration of the clinical disease condition, and the 10 mg/kg ibudilast-treated group showed significant amelioration. Moreover, in the ibudilast-treated group, the disease onset was delayed (FIG. 1).

Figure 2:
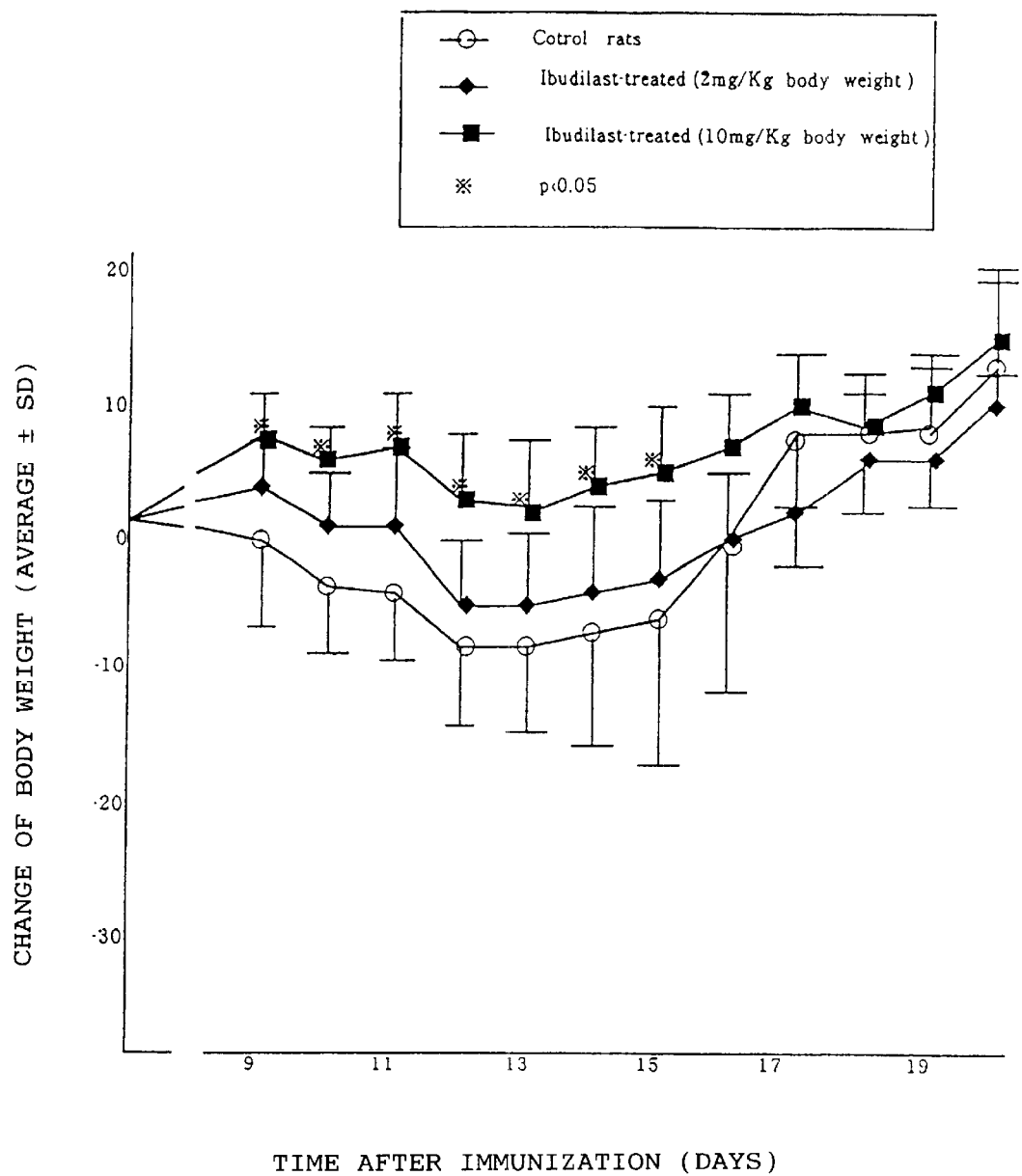
FIG. 2 is a graph showing the change of the body weight in Example 1 on each time after immunization.

The rats of the 10 mg/kg-treated group which were improved significantly in clinical disease conditions were suppressed significantly from body weight decrease (FIG. 2).

Thus the ibudilast showed a disease ameliorating effect and a body weight decrease prevention effect.

Example 2

The effect of ibudilast for rats of a multiple sclerosis model (EAE model) was investigated pathologically.
(1) Experimental Animal: DA Strain Rats (3 Rats in Each Group)
(2) Preparation of Model The rats were injected subcutaneously with a Freund's complete adjuvant containing H37Ra Mycobacterium tuberculosis, and Myelin basic protein (MBP).

The rats of the control group were injected merely with the Freund's complete adjuvant.
(3) Method of Dosing Ibudilast was administered through a feeding tube at a dosage of 10 mg/kg once a day, which dosage showed the significant effect of ameliorating the disease condition. The rats of the control group were dosed with physiological saline in the same manner.
(4) Histological Evaluation Twelve days after the immunization, the rats of ibudilast-treated group and of the control group were anesthetized and were fixed with paraformaldehyde by transcardiac transfusion, and the lumbar part of spinal cord was stained with hematoxylin-eosin to evaluate the extent of inflammation.
(5) Evaluation of Effect (Histological Score)

Score 0: Normal

Score 1: Inflammatory cell cuffing limited to the perivascular spaces

Score 2: A few infiltration of inflammatory cells into spinal cord parenchyma

Score 3: Considerable infiltration of inflammatory cells into spinal cord parenchyma Score 4: Marked infiltration of inflammatory cells into spinal cord parenchyma with destruction of the gray matter
(6) Result The average score of the 10 mg/kg ibudilast-treated group was about 2.0, whereas that of the control group was 3.5.

Ibudilast showed significant effect histologically in comparison with the control (FIG. 3).

This result supports the results of the experiment in [Example 1] of amelioration of clinical disease conditions.

INDUSTRIAL APPLICABILITY

Ibudilast is confirmed to be effective to the EAE model. Therefore, it is useful as a remedy for multiple sclerosis with safety higher than that of steroids with a medical cost lower than that of interferon β.

What is claimed is:

1. A method of treating multiple sclerosis comprising oral administration of a medicine containing an effective multiple sclerosis treating amount of ibudilast to a subject in need thereof wherein ibudilast is represented by the chemical formula:

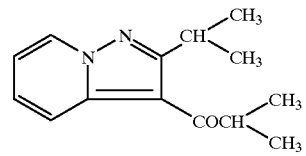

* * * * *